(12) United States Patent
Wenchell

(10) Patent No.: US 9,192,291 B2
(45) Date of Patent: Nov. 24, 2015

(54) ANOSCOPE

(71) Applicant: Covidien LP, Mansfield, MA (US)

(72) Inventor: Thomas Wenchell, Durham, CT (US)

(73) Assignee: Covidien LP, Mansfield, MA (US)

( * ) Notice: Subject to any disclaimer, the term of this patent is extended or adjusted under 35 U.S.C. 154(b) by 0 days.

(21) Appl. No.: 14/551,709

(22) Filed: Nov. 24, 2014

(65) Prior Publication Data
US 2015/0080656 A1 Mar. 19, 2015

Related U.S. Application Data

(63) Continuation of application No. 13/709,576, filed on Dec. 10, 2012, now Pat. No. 8,926,505, which is a continuation of application No. 12/620,535, filed on Nov. 17, 2009, now Pat. No. 8,348,837.

(60) Provisional application No. 61/120,926, filed on Dec. 9, 2008.

(51) Int. Cl.
| A61B 1/32 | (2006.01) |
| A61B 1/31 | (2006.01) |
| A61B 17/34 | (2006.01) |
| A61B 1/00 | (2006.01) |
| A61M 29/00 | (2006.01) |

(52) U.S. Cl.
CPC .............. *A61B 1/31* (2013.01); *A61B 1/0008* (2013.01); *A61B 1/00154* (2013.01); *A61B 17/3439* (2013.01); *A61M 29/00* (2013.01); *A61B 2017/3452* (2013.01)

(58) Field of Classification Search
CPC .................. A61B 2017/3452; A61M 29/00
USPC .............. 600/184–246, 38; 403/359.1, 359.4, 403/359.6; 601/46–147; 606/108, 191, 197, 606/198
See application file for complete search history.

(56) References Cited

U.S. PATENT DOCUMENTS

| 295,798 | A | | 3/1884 | Pagett | |
| 314,132 | A | | 3/1885 | Ingersoll | |
| 348,843 | A | * | 9/1886 | Hamilton | A61B 1/31 600/184 |
| 357,216 | A | | 2/1887 | McCall | |
| 395,705 | A | * | 1/1889 | King | A61B 1/31 600/184 |
| 457,787 | A | * | 8/1891 | Leisenring | A61B 1/31 600/184 |
| 1,286,083 | A | * | 11/1918 | Pennington | A61B 1/31 600/184 |
| 2,290,571 | A | | 7/1942 | Peyton | |

(Continued)

FOREIGN PATENT DOCUMENTS

| DE | 3717607 A1 | 12/1988 |
| EP | 1929959 A1 | 6/2008 |
| WO | 2009092194 A1 | 7/2009 |

OTHER PUBLICATIONS

PCT International Search Report for PCT/IT2005/000619 filed on Oct. 26, 2005 in the name of Carlo Rebuffat, et al.

*Primary Examiner* — Eduardo C Robert
*Assistant Examiner* — Stuart S Bray

(57) ABSTRACT

An anoscope kit includes an anoscope having a plurality of spaced apart fingers having free ends and a dilator removably positionable within the anoscope to aid insertion of the anoscope. The dilator has a proximal region, an intermediate region and a distal region. The distal region includes an enlarged distal head. A ramped surface extends from the enlarged distal head toward the intermediate region. The intermediate region has an outer surface to contact the fingers of the dilator.

11 Claims, 6 Drawing Sheets

(56) References Cited

U.S. PATENT DOCUMENTS

| | | | |
|---|---|---|---|
| 2,469,880 A | 5/1949 | Kowan | |
| 2,754,822 A | 7/1956 | Emelock | |
| 2,769,441 A | 11/1956 | Abramson | |
| 2,922,415 A * | 1/1960 | Campagna | A61B 1/31 600/184 |
| 3,051,176 A | 8/1962 | Albertl et al. | |
| 3,132,645 A | 5/1964 | Gasper et al. | |
| 3,459,175 A | 8/1969 | Miller | |
| 3,701,347 A | 10/1972 | Belkin | |
| 3,750,424 A * | 8/1973 | Nettleton | F16D 1/101 192/71 |
| 4,220,155 A * | 9/1980 | Kimberling | A61B 17/320016 606/137 |
| 4,341,211 A | 7/1982 | Kline | |
| 4,475,737 A * | 10/1984 | Cook, Jr. | F16C 3/03 206/318 |
| 4,538,594 A * | 9/1985 | Boebel | A61B 1/31 600/102 |
| 4,834,067 A * | 5/1989 | Block | A61B 1/31 600/184 |
| 4,957,486 A * | 9/1990 | Davis | A61B 1/31 600/106 |
| 4,957,499 A * | 9/1990 | Lipatov | A61B 17/115 227/180.1 |
| 5,122,149 A | 6/1992 | Broome | |
| 5,144,860 A * | 9/1992 | Furuhashi | B60R 16/027 200/61.27 |
| 5,176,127 A | 1/1993 | Dormia | |
| 5,235,966 A | 8/1993 | Jamner | |
| 5,256,149 A | 10/1993 | Banik et al. | |
| 5,320,587 A * | 6/1994 | Bodtker | F16H 48/08 29/432 |
| 5,351,674 A | 10/1994 | Hawks | |
| D353,197 S | 12/1994 | Hawks | |
| 5,404,870 A * | 4/1995 | Brinkerhoff | A61B 17/00 227/175.1 |
| 5,425,736 A | 6/1995 | Wadsworth | |
| D360,261 S | 7/1995 | Swanson et al. | |
| 5,464,412 A | 11/1995 | Budding | |
| 5,505,690 A | 4/1996 | Patton et al. | |
| 5,509,893 A | 4/1996 | Pracas | |
| D384,412 S | 9/1997 | Mainiero | |
| 5,716,329 A | 2/1998 | Dieter | |
| 5,741,273 A | 4/1998 | O'Regan | |
| 5,916,150 A | 6/1999 | Sillman | |
| 5,931,776 A | 8/1999 | Dotolo | |
| 5,957,902 A * | 9/1999 | Teves | A61B 1/07 600/184 |
| 6,083,241 A * | 7/2000 | Longo | A61B 17/0293 227/179.1 |
| 6,102,271 A * | 8/2000 | Longo | A61B 17/0293 227/175.1 |
| 6,126,594 A * | 10/2000 | Bayer | A61B 1/31 600/184 |
| 6,136,009 A | 10/2000 | Mears | |
| 6,142,931 A * | 11/2000 | Kaji | A61B 1/31 600/102 |
| 6,142,933 A | 11/2000 | Longo et al. | |
| 6,152,936 A | 11/2000 | Christy et al. | |
| 6,315,713 B1 | 11/2001 | Takada | |
| 6,364,852 B1 | 4/2002 | Lee | |
| 6,428,473 B1 * | 8/2002 | Leonard | A61B 1/31 600/219 |
| 6,458,077 B1 * | 10/2002 | Boebel | A61B 1/12 600/114 |
| 6,497,654 B1 | 12/2002 | Leonard et al. | |
| 6,503,192 B1 | 1/2003 | Ouchi | |
| 6,506,157 B1 | 1/2003 | Teigman et al. | |
| 6,547,798 B1 | 4/2003 | Yoon et al. | |
| 6,616,603 B1 | 9/2003 | Fontana | |
| 6,685,572 B2 * | 2/2004 | Makino | F16D 1/06 403/359.6 |
| 6,702,741 B2 | 3/2004 | Rioux et al. | |
| 6,740,098 B2 | 5/2004 | Abrams et al. | |
| 6,740,101 B2 | 5/2004 | Houser et al. | |
| 6,761,687 B1 | 7/2004 | Doshi et al. | |
| 7,029,438 B2 | 4/2006 | Morin et al. | |
| 7,037,314 B2 * | 5/2006 | Armstrong | A61B 1/31 606/1 |
| 7,118,528 B1 * | 10/2006 | Piskun | A61B 1/31 227/175.1 |
| 7,172,510 B2 * | 2/2007 | Fuhrmann | B21K 1/762 403/359.6 |
| D564,657 S | 3/2008 | Tsai | |
| 7,452,329 B2 * | 11/2008 | Bastia | A61B 1/00105 600/105 |
| 7,611,458 B2 | 11/2009 | Sias | |
| 8,206,292 B2 | 6/2012 | Eckman | |
| 8,348,837 B2 | 1/2013 | Wenchell | |
| 8,485,798 B2 * | 7/2013 | Sheth | F04D 13/022 403/300 |
| 8,585,719 B2 | 11/2013 | Chen et al. | |
| 8,708,897 B2 | 4/2014 | Braga et al. | |
| 2003/0069472 A1 | 4/2003 | Butler | |
| 2003/0130559 A1 * | 7/2003 | Morin | A61B 1/00073 600/104 |
| 2004/0015051 A1 * | 1/2004 | Sudakov | A61B 1/31 600/105 |
| 2004/0260152 A1 | 12/2004 | Sant et al. | |
| 2005/0277811 A1 * | 12/2005 | Richards | A61B 1/303 600/184 |
| 2006/0009797 A1 * | 1/2006 | Armstrong | A61B 1/00071 606/197 |
| 2006/0036129 A1 | 2/2006 | Sias | |
| 2006/0212046 A1 * | 9/2006 | Pearce | A61B 17/12009 606/140 |
| 2006/0264706 A1 * | 11/2006 | Piskun | A61B 1/31 600/105 |
| 2007/0043264 A1 | 2/2007 | Gillis et al. | |
| 2007/0104535 A1 * | 5/2007 | Valovick | F16C 3/03 403/359.1 |
| 2007/0135679 A1 * | 6/2007 | Hunt | A61B 1/00154 600/102 |
| 2008/0091218 A1 | 4/2008 | Richardson | |
| 2008/0097478 A1 | 4/2008 | Doughty et al. | |
| 2008/0262511 A1 * | 10/2008 | Delaney | A61B 1/31 606/115 |
| 2008/0275306 A1 * | 11/2008 | Rebuffat | A61B 1/31 600/184 |
| 2008/0319269 A1 * | 12/2008 | Longo | A61B 17/02 600/235 |
| 2009/0005647 A1 * | 1/2009 | Bozdag | A61B 1/31 600/235 |
| 2009/0012356 A1 | 1/2009 | Dann et al. | |
| 2009/0124862 A1 * | 5/2009 | Cohen | A61B 1/00154 600/235 |
| 2009/0187079 A1 * | 7/2009 | Albrecht | A61B 1/32 600/206 |
| 2009/0192352 A1 * | 7/2009 | Regadas | A61B 17/3462 600/114 |
| 2009/0203961 A1 | 8/2009 | Regadas | |
| 2009/0259110 A1 * | 10/2009 | Bastia | A61B 1/31 600/235 |
| 2009/0306586 A1 * | 12/2009 | Ross | A61B 17/3439 604/93.01 |
| 2010/0023023 A1 * | 1/2010 | Popovic | A61B 17/0643 606/142 |
| 2010/0145148 A1 | 6/2010 | Wenchell | |
| 2011/0087075 A1 * | 4/2011 | Wenchell | A61B 1/00154 600/235 |

* cited by examiner

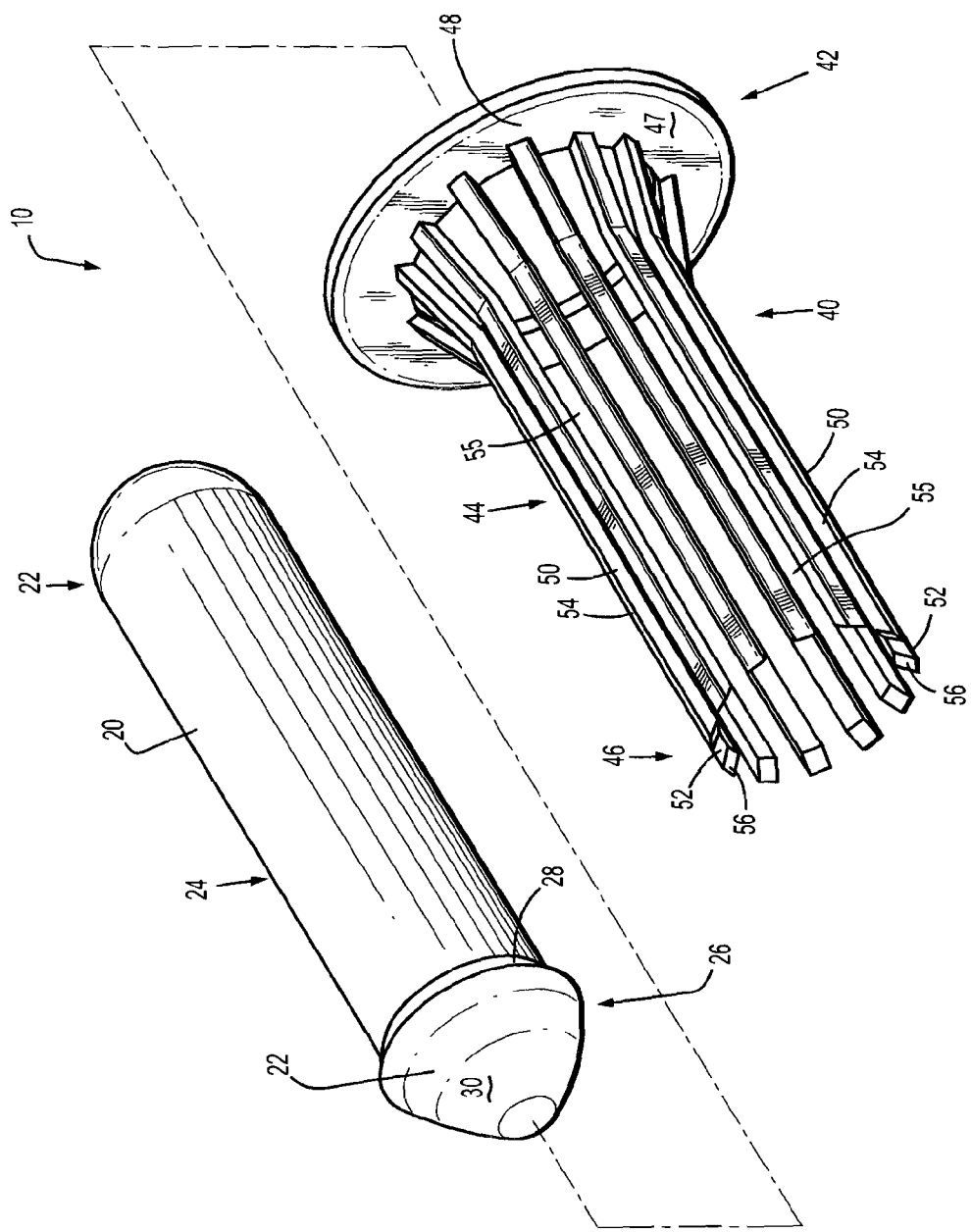

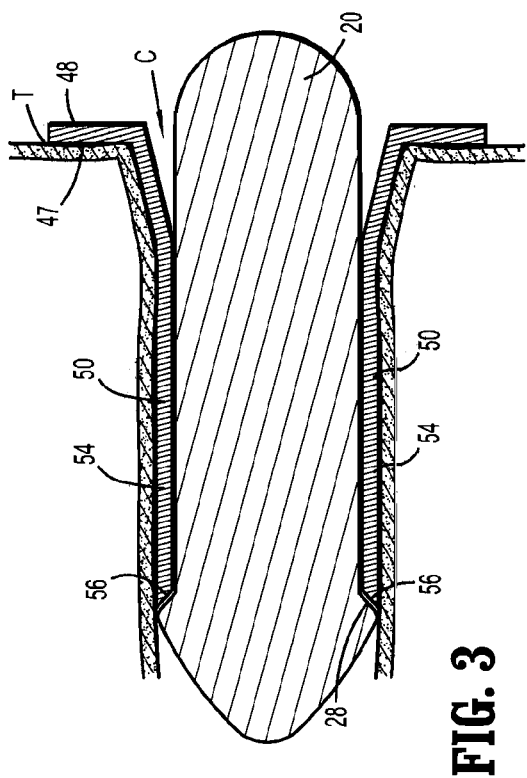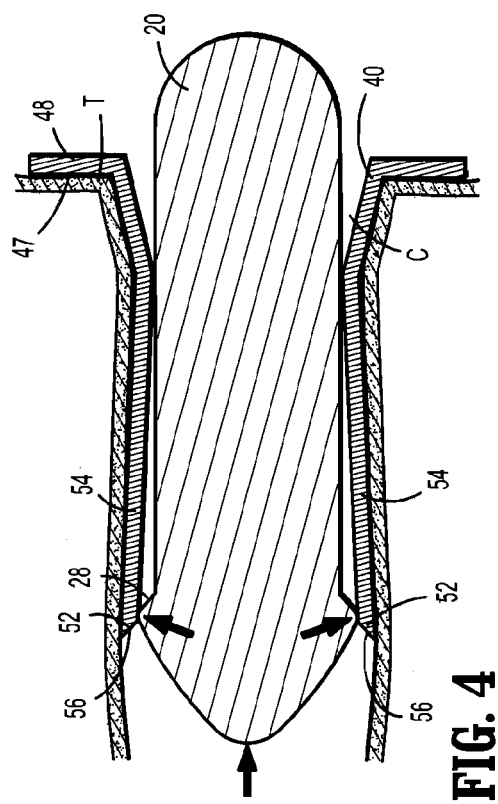

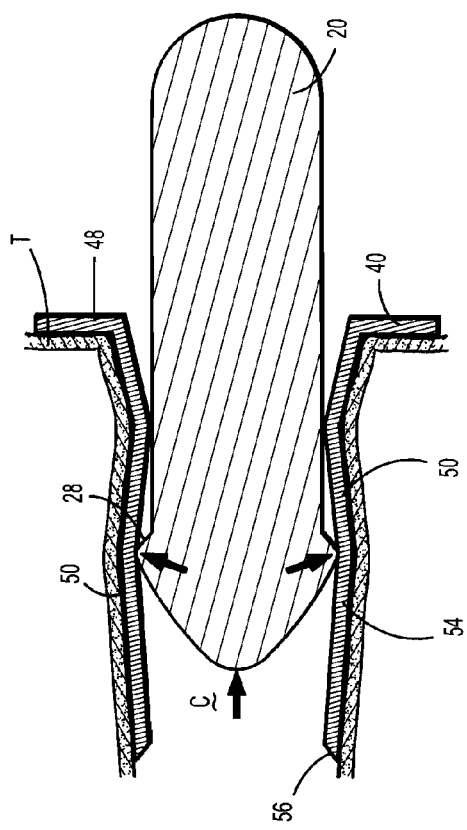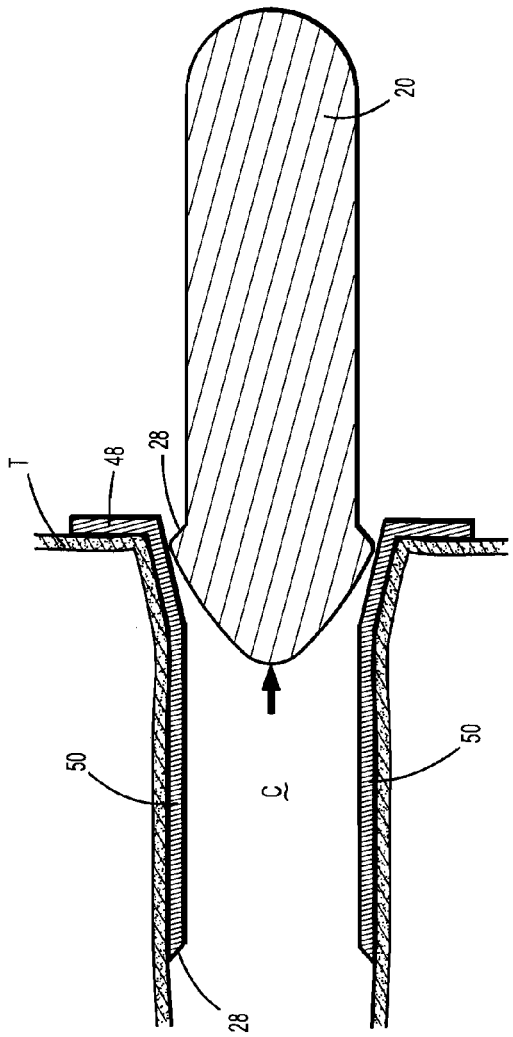

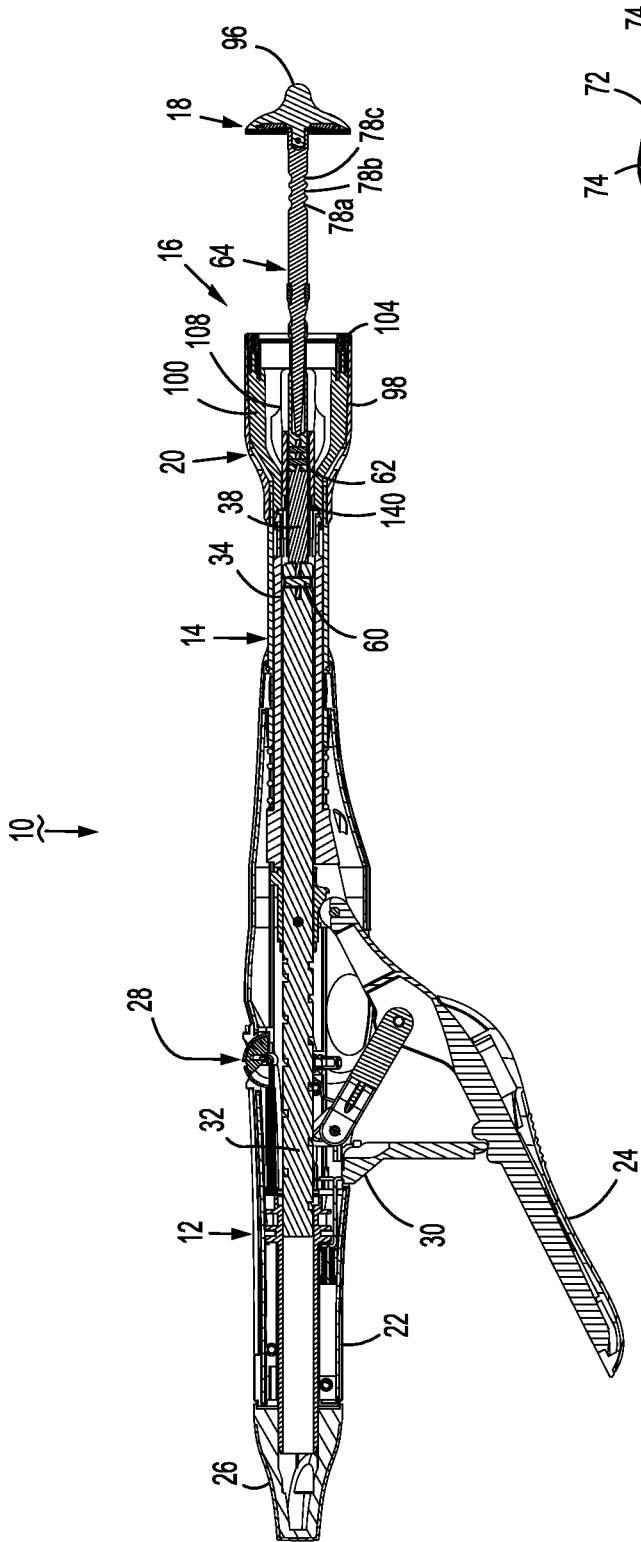
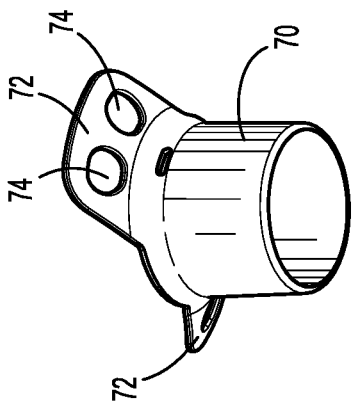
FIG. 7
FIG. 8

ANOSCOPE

CROSS-REFERENCE TO RELATED APPLICATIONS

This application is a continuation of U.S. patent application Ser. No. 13/709,576, filed on Dec. 10, 2012, which is a continuation of U.S. patent application Ser. No. 12/620,535, now U.S. Pat. No. 8,348,837, filed on Nov. 17, 2009, which claims the benefit of, and priority to, U.S. Provisional Patent Application Ser. No. 61/120,926, filed on Dec. 9, 2008, the entire content of each of the applications identified above being incorporated by reference herein.

BACKGROUND

1. Technical Field

The present disclosure relates to an anoscope for use in surgical procedures.

2. Background of Related Art

An anoscope is a device for providing access to the anal canal and lower rectum. It is generally a tubular device that is inserted into the anus and dilates the anus to provide an access passage. In some instances, the anoscope provides a passage for a suturing device to apply purse string sutures to the desired tissue. One common application is for hemorrhoid surgery where the hemorrhoid or adjacent tissue is accessed through the anoscope and purse stringed for subsequent clamping in a circular stapling device which resects and staples the tissue.

The need exists for an improved anoscope to enhance access to the anal canal and enhance application of purse string sutures for hemorrhoid or other surgical procedures.

SUMMARY

There is disclosed an anoscope kit having an anoscope and dilator. The anoscope has a proximal portion, a distal portion, and a plurality of spaced apart fingers having free ends. The dilator is removably positionable within the anoscope to aid insertion thereof and has a proximal region, an intermediate region and a distal region. The distal region of the dilator includes an enlarged distal head, and a ramped surface extends from the enlarged distal head toward the intermediate region. The intermediate region has an outer surface to contact the fingers of the anoscope.

In one embodiment, the fingers of the anoscope extend substantially parallel to a longitudinal axis of the anoscope and the free ends of the fingers extend substantially parallel to the longitudinal axis of the anoscope. In one embodiment, the free ends of the fingers lie in substantially the same plane as an intermediate portion of the finger.

The anoscope may include a flange at the proximal portion. In a preferred embodiment, the transverse dimension of the anoscope at the region of the fingers is substantially equal to a largest cross-sectional dimension of the distal head of the dilator.

The kit may further include a port dimensioned to receive the anoscope.

In one embodiment, the fingers extend inwardly towards a distal end such that a first transverse dimension of the anoscope adjacent a distal end of the fingers is less than a second transverse dimension of the anoscope at a proximal end of the fingers. In this embodiment, preferably the transverse dimension of the enlarged head is greater than the first dimension and less than the second dimension.

The present disclosure also provides in combination an anoscope and dilator wherein the dilator has a distal head forming an enlarged head region, an intermediate region having an outer surface configured to abut fingers of the anoscope, and a transition surface from the distal head to the intermediate region. The anoscope has a plurality of fingers separated to form gaps therebetween, a portion of the fingers dimensioned to lie on the transition surface and on the intermediate region of the dilator.

In a preferred embodiment, a distal tip of the fingers lies on the transition surface of the dilator. In one embodiment, the transition surface is a ramped surface. The distal tips of the fingers have an angled surface engaging the ramped surface of the dilator when the dilator is positioned within the anoscope.

The anoscope may include an enlarged proximal region creating a stop for insertion of the anoscope into the anal canal.

The present disclosure also provides a method of inserting an anoscope into a patient comprising the steps of:

providing a dilator having an enlarged dilating distal head forming a lip;

providing an anoscope having a plurality of fingers extending substantially parallel to a longitudinal axis of the anoscope;

inserting the dilator into the anoscope; and advancing the dilator and anoscope into an anal canal of the patient wherein distal tips of the fingers abut the lip of the dilator to thereby reduce flexing of the fingers during anoscope insertion.

DESCRIPTION OF THE DRAWINGS

Embodiments of the presently disclosed anoscope and dilator are disclosed herein with reference to the drawings, wherein:

FIG. 2 is a perspective view of the anoscope and dilator prior to insertion of the dilator within the anoscope;

FIG. 3 is a cross-sectional view illustrating the dilator within the anoscope positioned within the anal canal;

FIG. 4 is a cross-sectional view similar to FIG. 3 showing initial withdrawal of the dilator from within the anoscope;

FIG. 5 is a cross-sectional view similar to FIG. 4 showing the dilator further withdrawn from the anoscope;

FIG. 6 is a cross-sectional view similar to FIG. 5 showing the dilator being withdrawn from the anoscope;

FIG. 7 is a perspective view of a port for optional use with the anoscope of the present disclosure; and FIG. 8 is a side view in partial cross section of a surgical stapler.

DETAILED DESCRIPTION OF EMBODIMENTS

Figure 1:
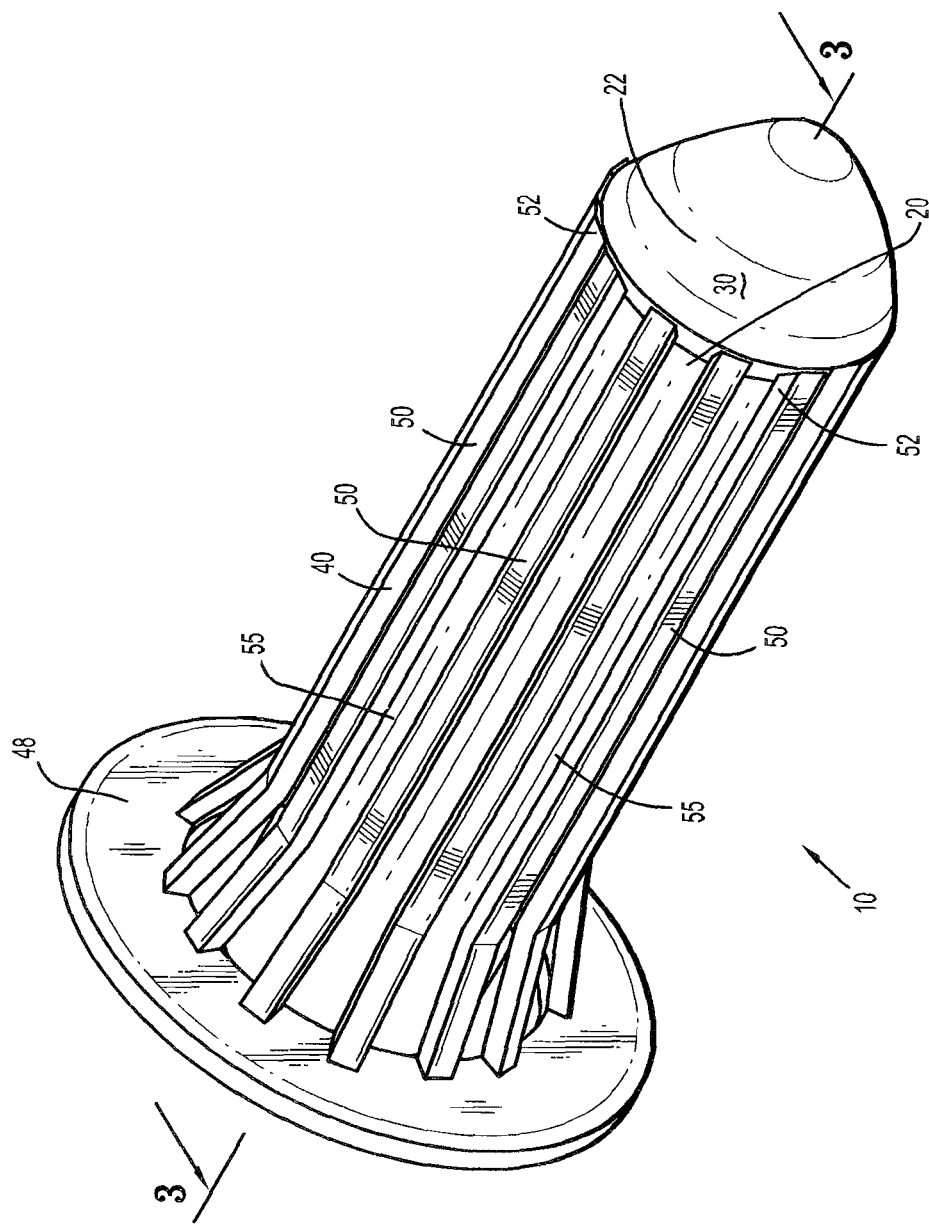
FIG. 1 is a perspective view of one embodiment of an anoscope and dilator of the present disclosure showing the dilator positioned within the anoscope.

The anoscope kit of the present disclosure will now be described in detail with reference to the drawings wherein like reference numerals designate identical or corresponding elements in each of the several views. As is common in the art, the term 'proximal" refers to that part or component closer to the user or operator, i.e. surgeon or physician, while the term "distal" refers to that part or component further away from the user.

It should be appreciated that the anoscope can be used in a variety of surgical procedures. Such procedures include, for example, the treatment of colon prolapse and hemorrhoids.

Some of the procedures, such as hemorrhoid procedures, require application of a purse string suture to the hemorrhoids. In other procedures, such as hemorrhoidopexy, a purse string suture is applied to tissue adjacent the hemorrhoids. The anoscope disclosed herein aids the application of such sutures. After application of the purse string, the anoscope is removed and a surgical stapler can be inserted into the anal canal. One such stapler which can be utilized, for example, is disclosed in commonly assigned copending application Ser. No. 12/550,443, filed Aug. 31, 2009 (the "443 application"), the entire contents of which is incorporated herein by reference. The stapler is also shown in FIG. 8 of the present disclosure. As described in that application, the surgical stapler 10 includes a handle assembly 12, a central body portion 14 and a distal head portion 16. Head portion 16 includes an anvil assembly 18 and a shell assembly 20. Handle assembly 12 includes a stationary handle 22, a firing trigger 24, an approximation knob 26, an indicator assembly 28, and a lockout mechanism 30. Approximation knob 26 functions to retract and advance a drive screw 32 and anvil retainer (connected by connector 38 via screws 60, 62) to advance or retract anvil assembly 18 in relation to cartridge assembly 20. Firing trigger 24 functions to advance a pusher link 34 to eject staples from shell assembly 20 advanced by pusher fingers 104. Shell assembly includes cylindrical portion 98. Each of the components of handle assembly 12 identified above are substantially as described in the '443 application and U.S. Pat. No. 7,303,106 ("'106 patent"). The '106 patent is incorporated herein in its entirety by reference. Accordingly, these components and assemblies are not described in detail herein.

As discussed above, the stapler 10 is particularly suitable for use in surgical procedures for treating colon prolapse or hemorrhoids. During such procedure, an access port can be inserted into the anus to facilitate access to the prolapsed colon or hemorrhoids. Next, a purse string suture (not shown) is placed into, above or in the vicinity of the colon prolapse and the anvil assembly 18 is inserted through the access port into the anus and rectum. Bulbous member 96 functions to allow smooth passage of anvil assembly 18 past the purse string suture. Thereafter, a purse string suture 32 is placed through anvil shaft or center rod 64 in one of holes 78a, 78b 78c. Holes 78 are longitudinally spaced along shaft 64 such that the amount of tissue drawn into the shell assembly 20 can be controlled by properly selecting the hole 78 to which the purse string suture is inserted. A greater amount of tissue will be drawn into shell assembly 20 by attaching the purse string suture to the proximal most hole 78. Anvil assembly 18 and shell assembly 20 are then approximated via knob 26 to draw the prolapsed colon into shell assembly 20.

When surgical stapler 10 is fully approximated, firing trigger 24 can be actuated or fired in a manner described in the '106 patent to staple, sever and allow removal of a portion of the prolapsed colon. Thereafter, stapler 10 is removed from the anus with the excised tissue contained within a receptacle of pusher back 100 within shell assembly 20.

FIGS. 1 and 2 illustrate the components of a preferred embodiment of the anoscope kit 10 of the present disclosure useful for hemorrhoid or other surgical procedures including facilitating application of purse string sutures. Kit 10 includes a dilator 20 with a dilating tip 22 and an anoscope 40. The dilator 20 is shown in FIG. 1 inserted within the anoscope 40. Anoscope 40 can optionally be composed of transparent material to facilitate visualization of the surgical site, e.g. the hemorrhoidal tissue and adjacent tissue when used in a hemorrhoidectomy procedure.

Dilator 20 includes a proximal portion or region 22, an intermediate portion or region 24 and a distal portion or region 26. Distal portion 26 includes an enlarged distal head 30, preferably substantially conical in configuration, which has a dilating tip 22 to aid insertion of the anoscope 40. The intermediate portion 24 has a transverse dimension, e.g. diameter, smaller than the largest diameter of the head portion 30, thus forming a reduced diameter region proximal of the lip of the distal head 22. A transition surface 28 joins intermediate portion 24 with enlarged head 30. In a preferred embodiment, transition surface 28 is angled toward the intermediate portion 24 to form a ramped surface as described below. The dilator 20 is removably positioned in the anoscope 40; its positioning within the anoscope 40 aiding insertion of the anoscope 40 through the anus and into the anal canal.

Anoscope 40 has a proximal portion or region 42, an intermediate portion or region 44 and a distal portion or region 46. The proximal portion 42 includes a flange 48 which provides a stop to prevent full insertion of the anoscope 40 into the anal canal. This is shown for example in FIG. 3 wherein the transverse dimension of the flange 48 exceeds the dimension of the anal opening; the inner surface 47 of flange 48 contacting the tissue region T adjacent the anal opening.

Extending from the inner surface 47 of flange 48 are a plurality of fingers 50. Fingers 50 are composed of flexible material to enable the fingers to flex during removal of the dilator 20 as discussed below. The fingers 50 are spaced apart forming gaps 55 therebetween to facilitate application of purse string sutures around a 360 degree area as the tissue, e.g. hemorrhoid tissue, can be accessed through the gaps 55 between the fingers 50. Thus, purse string sutures can be applied to the necessary tissue, e.g. hemorrhoidal tissue, without rotation of the anoscope 40. Note that for clarity, only some of the fingers are labeled, it being understood that the unlabeled fingers have corresponding parts.

Fingers 50 terminate in distal tips 52. After extending inwardly from flange 48, the fingers 50 extend substantially parallel to a longitudinal axis of the anoscope and the free distal ends of the fingers extend substantially parallel to the longitudinal axis of the anoscope. The fingers 50 as shown extend longitudinally in a plane with the distal tip 52 preferably lying substantially in the same plane as the intermediate regions 54 of the respective finger. Stated another away, the distance between the intermediate portions of opposing fingers 50 and the distal portions of those fingers remains substantially the same.

The distal tips 52 of the fingers preferably have an angled or ramped surface 56. This angled surface corresponds in angle to the ramped surface of transition surface 28 of dilator 20. Thus, a substantially flush and smooth surface is formed as the fingers 50 (or at least a portion thereof) lie on the reduced diameter portion (proximal of the distal head 22) of the dilator 20. Stated another away, when the dilator 20 is positioned within the anoscope 40, the transverse dimension of the finger region is substantially equal to the largest outer dimension of the dilator 20, i.e. the outer dimension of the head portion 30. This provides a smooth surface for insertion. By abutting the lip of the distal head 22, the distal tips 52 of the fingers 50 are shielded by the lip to prevent flexing at the tips during insertion.

Use of the anoscope/dilator kit of the present disclosure is shown in FIGS. 3-6. As shown in FIG. 3, the dilator is positioned within the anoscope 40 and positioned within the anal canal C. As shown, the angled surface 56 of fingers 50 abut the respective ramped surface 28 of the dilator 20, terminating flush with the lip of the distal head. This mating of the surfaces creates a smooth insertion surface as shown in FIG. 3, with the lip shielding the distal end of the fingers 50 to reduce flexing of the fingers 50 during insertion. After insertion of the anoscope 40 with the aid of the dilator 20 and dilating tip 22, the dilator 20 is removed. As shown in FIG. 4, retraction (withdrawal) of the dilator 20 in the direction of the arrow, cams the fingers 50 outwardly, as the ramped surface 56 slides past the ramped surface 28 of the dilator. This outward flexing of the fingers 50 continues, as shown in FIG. 5, until the dilator 20 is withdrawn to the position of FIG. 6. The dilator 20 is then completely removed from the anoscope 40, with the anoscope 40 left in place for insertion of instrumentation to apply purse string sutures. As noted above, purse string sutures can be applied to the tissue by accessing the tissue through the gaps 55 between the fingers 50.

Figure 6A:
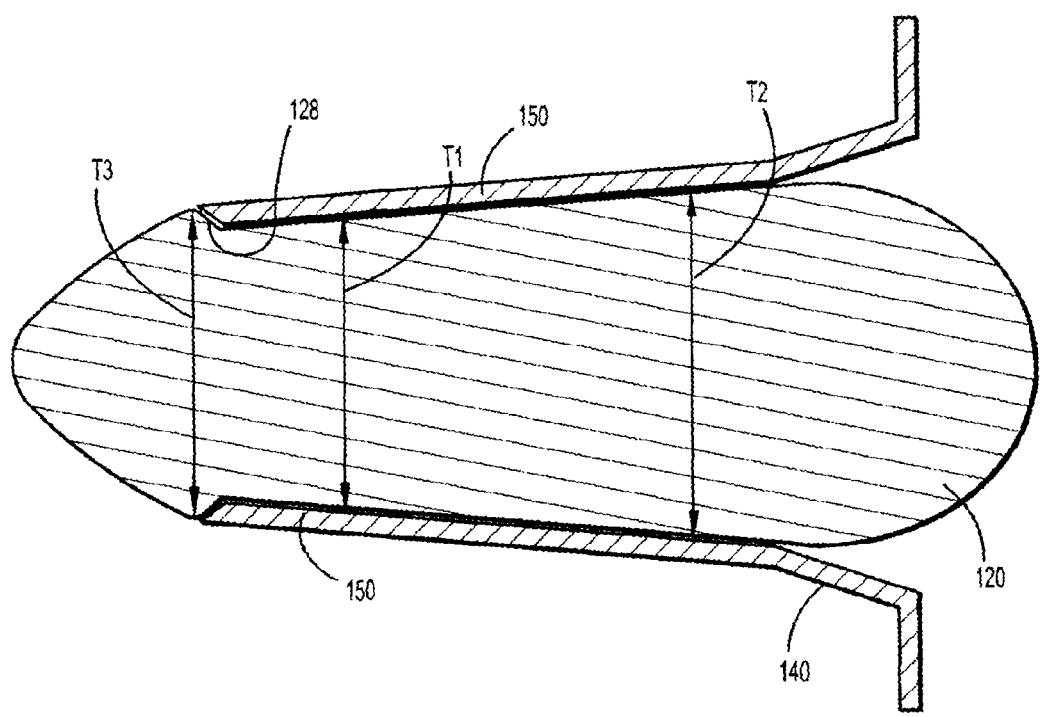
FIG. 6A is a cross-sectional view of an alternate embodiment of the dilator and anoscope showing the dilator positioned within the anoscope.

In an alternative embodiment shown in FIG. 6A, the fingers 150 of the anoscope 140 taper inwardly (in a distal direction) along their length so that the transverse dimension of the fingers at the distal region, e.g. dimension T1, is less than the transverse dimension at the proximal region, e.g. dimension T2. Similarly, the dilator 120 can be tapered inwardly in a distal direction in the region proximal of the enlarged distal head 122. The angled surfaces of fingers 150 abut the ramped surface 128 of the dilator in the same manner as in the embodiment of FIG. 1. Also, the enlarged head 122 has a cross-sectional (transverse) dimension T3 greater than the transverse dimension of the fingers at the distal end (T1) (to form a lip to shield the tips) but less than the transverse dimension at the proximal end (T2). In this manner, after the dilator 120 is withdrawn a sufficient distance within the anoscope 140, the dilator can be more easily removed as the enlarged head 122 reaches the larger transverse dimension of the fingers 150 and can more freely slide through the anoscope 140 as deflection of the fingers 150 is no longer necessary. In preferred embodiments, the dimensions provided would be such that when the dilator is removed one half way or three-quarters of the way through the anoscope, it becomes in clearance and the fingers no longer need to deflect, especially down near the base where the dilator would be stiffer. Other distances are also contemplated.

Note that optionally a port can be provided such as shown in FIG. 7. Port 70 has an opening dimensioned to receive the anoscope 40 (and inserted dilator 20) and wings 72 with suture holes 74 for attachment to the skin of the patient.

In use, the anoscope 40 (or anoscope 140) with dilator 20 (or dilator 120) positioned therein is inserted within the port 70 for access to the anal canal. That is, the anoscope 40 is positioned coaxially within port 70 and obturator 20 is positioned coaxially within anoscope 40. The unit, containing the three coaxial components, is inserted transanally. After insertion of the components, the obturator 20 is removed, leaving the anoscope 40 extending through port 70. A suture (not shown) extending through holes 74 attaches the port 70 to the patient's body. After removal of the obturator 20, a purse string suture is placed by the surgeon via a suture holder extending through the gaps 55 between the fingers 50 of anoscope 40. After the sutures are placed, the anoscope 40 is removed from the port 70 and the patient's body, leaving the port 70 in place to provide a passageway for instrumentation such as the hemorrhoid circular stapler described above. The stapling instrument, e.g. instrument 10 described above, can be inserted through the port 70 and attached to the anvil assembly. The anvil is then approximated and the instrument handle 24 actuated to fire the staples. After staple firing, the instrument is at least partially unapproximated and the instrument and attached anvil are withdrawn. It should be appreciated that these three components (anoscope, dilator and port) can be used for hemorrhoid surgery, treatment of colon prolapse as well as other surgical procedures.

It will be understood that various modifications may be made to the embodiments disclosed herein. Therefore, the above description should not be construed as limiting, but merely as exemplifications of preferred embodiments. Those skilled in the art will envision other modifications within the scope and spirit of the claims appended hereto.

The invention claimed is:

1. An anoscope defining a central longitudinal axis and comprising:
    a flange having a cannulated, disc-shaped configuration, the flange being configured to prevent full insertion of the anoscope into an anal canal; and
    a plurality of spaced apart fingers extending distally from the flange, each finger of the plurality of spaced apart fingers including:
    an inner surface;
    an outer surface; and
    a distal tip having an angled surface extending from the inner surface to the outer surface that tapers away from the central longitudinal axis in a distal direction, wherein the angled surface of the distal tip of each finger is planar.

2. The anoscope of claim 1, wherein the flange is configured to receive a dilator.

3. The anoscope of claim 1, wherein each finger of the plurality of spaced apart fingers further includes a proximal portion extending in parallel relation to the central longitudinal axis.

4. The anoscope of claim 1, wherein adjacent fingers of the plurality of spaced apart fingers define gaps, each gap extending longitudinally from the flange to the distal tip of each respective finger of the plurality of spaced apart fingers.

5. The anoscope of claim 1, wherein the plurality of spaced apart fingers is configured to flex outwardly relative to the central longitudinal axis upon receipt of a dilator within the anoscope.

6. A surgical system, comprising:
    an anoscope defining a central longitudinal axis and including:
        a flange having a cannulated, disc-shaped configuration, the flange being configured to prevent full insertion of the anoscope into an anal canal; and
        a plurality of spaced apart fingers extending distally from the flange, each finger of the plurality of spaced apart fingers including:
        an inner surface;
        an outer surface; and
        a distal tip having an angled surface extending from the inner surface to the outer surface that tapers away from the central longitudinal axis in a distal direction, wherein the angled surface of the distal tip of each finger is planar; and
    a dilator configured to be received through the flange, the dilator having a surface positioned to be in abutment with the angled surface of each finger of the plurality of spaced apart fingers of the anoscope upon receipt of the dilator in the anoscope.

7. The surgical system of claim 6, wherein the surface of the dilator tapers toward a central longitudinal axis of the dilator in a proximal direction.

8. The surgical system of claim 7, wherein the dilator further includes:
   an intermediate portion; and
   an enlarged distal head disposed distally of the intermediate portion, wherein the surface of the dilator is a transition surface interposed between the intermediate portion and the enlarged distal head.

9. The surgical system of claim 6, wherein each finger of the plurality of spaced apart fingers further includes a proximal portion extending in parallel relation to the central longitudinal axis.

10. The surgical system of claim 6, wherein adjacent fingers of the plurality of spaced apart fingers define gaps, each gap extending longitudinally from the flange to the distal tip of each respective finger of the plurality of spaced apart fingers.

11. The surgical system of claim 6, wherein the plurality of spaced apart fingers is configured to flex outwardly relative to the central longitudinal axis upon receipt of the dilator within the anoscope.

* * * * *